US00PP28703P3

(12) United States Plant Patent
Klemm et al.

(10) Patent No.: US PP28,703 P3
(45) Date of Patent: Nov. 28, 2017

(54) POINSETTIA PLANT NAMED 'NPCW15235'

(50) Latin Name: *Euphorbia pulcherrima*
Varietal Denomination: NPCW 15235

(71) Applicant: Klemm+Sohn GmbH & Co. KG, Stuttgart (DE)

(72) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 122 days.

(21) Appl. No.: 14/757,278

(22) Filed: Dec. 11, 2015

(65) Prior Publication Data

US 2017/0172042 P1 Jun. 15, 2017

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

(56) References Cited

PUBLICATIONS

PLUTO: Plant Variety Database, May 26, 2017, citation for 'NPCW15235'. 1 page.*

* cited by examiner

*Primary Examiner* — Susan McCormick Ewoldt
*Assistant Examiner* — Karen Redden
(74) *Attorney, Agent, or Firm* — Barbara Campbell; James M. Weatherly; Cochran Freund & Young, LLC

(57) ABSTRACT

A new poinsettia plant particularly distinguished by having red bracts, a triangular plant form, an upright growth habit, and excellent keeping quality, is disclosed.

1 Drawing Sheet

Genus and species: *Euphorbia pulcherrima.*
Variety denomination: 'NPCW15235'.

BACKGROUND OF THE NEW PLANT

The present invention comprises a new and distinct variety of poinsettia, botanically known as *Euphorbia pulcherrima* and hereinafter referred to by the variety name 'NPCW15235'. 'NPCW15235' was discovered in 2009 from an X-ray irradiation mutation of the parent variety 'NPCW07120' (U.S. Plant Pat. No. 20,222) which is commercially known as CHRISTMAS FEELINGS 'Pink'.

In May 2010, 'NPCW15235' was first asexually propagated by apical vegetative cuttings. 'NPCW15235' was found to reproduce true to type in successive generations of asexual propagation via apical vegetative cuttings in Stuttgart, Germany.

SUMMARY

The following are the most outstanding and distinguishing characteristics of this new variety when grown under normal horticultural practices in Stuttgart, Germany.

1. Red bracts;
2. A triangular plant form;
3. An upright growth habit; and
4. Excellent keeping quality.

CROSS-REFERENCE TO RELATED APPLICATIONS

An application with the European Community Plant Variety Office was filed for this variety on Jan. 20, 2015, File No. 2015/0139.

DESCRIPTION OF THE PHOTOGRAPH

This new poinsettia plant is illustrated by the accompanying photograph which shows an overall view of the plant. The photograph is of a plant approximately eleven-weeks-old grown indoors in Stuttgart, Germany in November 2014. The colors shown are as true as can be reasonably obtained by conventional photographic procedures.

DESCRIPTION OF THE NEW VARIETY

The following detailed descriptions set forth the distinctive characteristics of 'NPCW15235'. The data which define these characteristics were collected from asexual reproductions carried out in Stuttgart, Germany. Data was collected on nineteen-week-old plants (after potting) grown indoors in Stuttgart, Germany under greenhouse conditions in November 2015. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW15235'.

Parentage: Mutation from the poinsettia variety 'NPCW07120'.

Growth:
- *Time to produce a rooted cutting.*—4 weeks.
- *Blooming habit.*—Intermittent.
- *Flowering response time.*—Approximately 57 days.
- *Keeping quality.*—Excellent.

Plant description:

*Form.*—Triangular.

*Growth habit.*—Upright (broad angle).

*Height.*—22.0 cm to 27.0 cm.

*Width.*—25.0 cm to 30.0 cm.

*Number of branches.*—5 to 6.

*Average number of inflorescences per plant.*—5 to 6.

*Disease and pest resistance.*—None observed.

Propagation:

*Type cuttings.*—Apical cuttings.

*Time to produce a rooted cutting.*—4 weeks.

*Rooting habit and root color.*—Freely branching root habit; root color is RHS NN155D.

Lateral branches:

*Color.*—RHS 143A overlaid with RHS 183A.

*Length.*—About 22.0 cm.

*Internode length.*—1.0 cm to 4.0 cm.

*Diameter.*—0.5 cm to 1.0 cm.

*Branching habit.*—Freely branching.

*Number of lateral branches per plant.*—5 to 6.

*Texture.*—Smooth.

Leaves:

*Quantity.*—7 to 8 per lateral branch.

*Arrangement.*—Alternate.

*Number of lobes on the leaf blade.*—2 to 4.

*Lobation depth.*—Moderately deep.

*Depth of the deepest sinus of the leaf blade.*—Approximately 1.0 cm.

*Shape.*—Ovate.

*Apex.*—Acute.

*Base.*—Obtuse.

*Margin.*—Serrate.

*Length.*—7.0 cm to 11.0 cm.

*Width.*—4.0 cm to 7.0 cm.

*Texture* (*both surfaces*).—Smooth.

*Vein color.*—Upper surface: RHS 139A. Lower surface: RHS 181A to RHS 139D.

*Variegation.*—Absent.

*Venation pattern.*—Reticulate.

*Color.*—Mature foliage: Upper surface: RHS 139A. Lower surface: RHS 137B. Immature foliage: Upper surface: RHS 144B. Lower surface: RHS 143C.

*Leaf petiole.*—Length: 2.0 cm to 4.0 cm. Diameter: 0.2 cm to 0.3 cm. Color: Upper (part) surface: RHS 183A. Lower (part) surface: RHS 183A. Texture: Smooth. Strength: Medium.

Inflorescence:

*Lastingness of inflorescence on the plant.*—4 weeks.

*Natural flowering season.*—End of November.

*Diameter.*—16.0 cm to 21.0 cm.

*Height.*—2.0 cm to 5.0 cm.

*Fragrance.*—Absent.

Bracts:

*Number of bracts per inflorescence.*—6 to 8.

*Shape.*—Ovate.

*Apex.*—Acute.

*Base.*—Obtuse.

*Margin.*—Entire with occasional lobing.

*Size.*—Length: 8.0 cm to 11.0 cm. Width: 4.0 cm to 7.0 cm.

*Texture* (*both upper and lower surfaces*).—Smooth.

*Venation pattern.*—Reticulate.

*Vein color.*—Upper surface: RHS 185A. Lower surface: RHS 182B.

*Bract color.*—Upper surface: Close RHS 46B. Lower surface: Close to RHS 46C.

*Bract petiole.*—Length: 1.0 cm to 3.0 cm. Diameter: 0.2 cm. Color: Upper (part) surface: RHS 185A. Lower (part) surface: RHS 183A. Texture: Smooth. Strength: Medium.

Cyme:

*Diameter.*—1.5 cm.

*Cyathia number.*—4 to 7 per inflorescence.

*Deformation of glands of the cyathium.*—Absent.

*Cyathium.*—Shape: Ovoid. Diameter: 0.3 cm to 0.5 cm. Length: 0.4 cm to 0.7 cm. Color: RHS 143C.

*Peduncle.*—Color: RHS 144C. Length: 0.1 cm to 0.2 cm. Diameter: 0.2 cm. Texture: Smooth. Strength: Medium.

*Nectar cups.*—Number: 1 per cyathium. Diameter: 0.1 cm. Length: 0.2 cm to 0.3 cm. Color: RHS 13A to RHS 14C.

Reproductive organs:

*Stamen quantity.*—5 to 10 per cyanthium.

*Stamen shape.*—Ovoid.

*Filament length.*—0.2 cm.

*Filament color.*—RHS 46A.

*Pollen quantity.*—Moderate.

*Pollen color.*—RHS 9A to RHS 12A.

*Gynoecium.*—Present. Pistil quantity per cyathium: 1. Pistil length: 0.5 cm to 0.6 cm. Stigma form: divided in 2 parts. Stigma color: RHS 185 A. Style length: approx. 0.2 cm. Style color: RHS 185 A. Ovary length: 0.05 cm. Ovary color: RHS 143C.

Fruit and seed set: No fruit or seed observed.

COMPARISON WITH PARENTAL LINE AND KNOWN VARIETY

'NPCW15235' is distinguished from its parent 'NPCW07120' as described in Table 1.

TABLE 1

| Characteristic | Variety 'NPCW15235' | Parent 'NPCW07120' |
|---|---|---|
| Bract color | Upper surface is close RHS 46B Lower surface is close to RHS 46C | RHS 58C for both surfaces |
| Number of leaves per lateral branch | 7 to 8 | 8 to 15 |

'NPCW15235' can be compared to the commercial Poinsettia plant variety 'NPCW02044' (U.S. Plant Pat. No. 14,618). Differences between the two varieties are described in Table 2.

TABLE 2

| Comparison with Similar Variety | | |
|---|---|---|
| Characteristic | 'NPCW15235' | Commercial line 'NPCW02044' |
| Vigor | 10% higher | 10% lower |
| Diameter of inflorescence | 10% larger | 10% smaller |

We claim:

1. A new and distinct variety of poinsettia plant named 'NPCW15235' as illustrated and described herein.

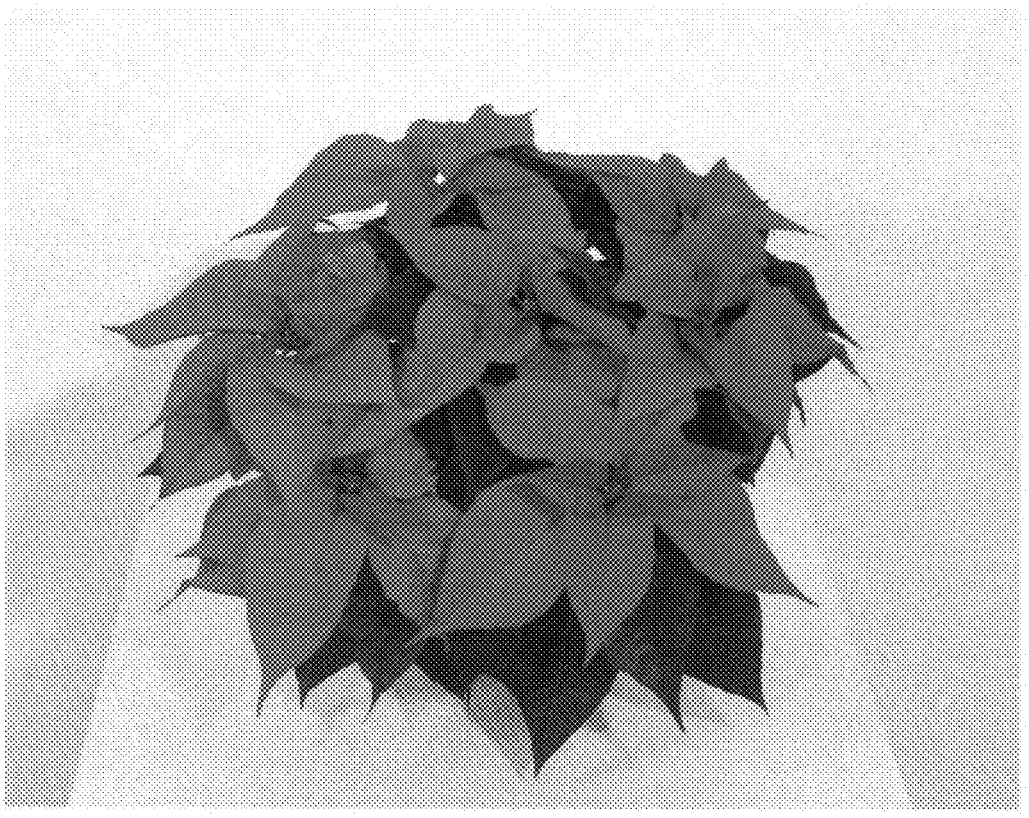

* * * * *